United States Patent [19]

Salinger

[11] Patent Number: 4,989,984
[45] Date of Patent: Feb. 5, 1991

[54] SYSTEM FOR MEASURING OPTICAL CHARACTERISTICS OF CURVED SURFACES

[75] Inventor: Jeremy A. Salinger, Southfield, Mich.

[73] Assignee: Environmental research Institute of Michigan, Ann Arbor, Mich.

[21] Appl. No.: 433,140

[22] Filed: Nov. 8, 1989

[51] Int. Cl.$^5$ ................ G01N 21/55; G01B 11/24
[52] U.S. Cl. ................................. 356/445; 356/376; 250/571
[58] Field of Search ...................... 356/445–448, 356/375–576, 380, 386, 387, 398, 45, 237; 250/563, 572, 571, 559, 275

[56] References Cited

U.S. PATENT DOCUMENTS

| | | | |
|---|---|---|---|
| 4,092,068 | 5/1978 | Lucas et al. | 356/376 |
| 4,139,307 | 2/1979 | Clarke | 356/446 |
| 4,158,507 | 6/1979 | Himmel | 356/376 |
| 4,247,204 | 1/1981 | Merlen et al. | 256/237 |
| 4,568,835 | 2/1986 | Imamura et al. | 356/446 |
| 4,569,078 | 2/1986 | Zuk | 328/134 |
| 4,687,326 | 8/1987 | Corlay, Jr. | 356/375 |
| 4,744,653 | 5/1988 | Sano et al. | 356/448 |
| 4,746,805 | 5/1988 | Stapleton | 356/446 |
| 4,785,186 | 11/1988 | Street et al. | 250/370.01 |

Primary Examiner—Richard A. Rosenberger
Assistant Examiner—Hoa Pham
Attorney, Agent, or Firm—Krass & Young

[57] ABSTRACT

A system for evaluating the optical characteristics of curved surfaces includes a light source disposed to scan a beam of light across a surface and ranging means for measuring the distance from the light source to the point being scanned and a controller for controlling the position of the light beam with regard to the measured distance so as to maintain reflected illumination upon a detector. By analysis of the profile of the reflected light, parameters such as gloss, distinctness of image, orange peel and surface roughness may be readily determined.

20 Claims, 3 Drawing Sheets

FIG-5
_PRIOR ART_
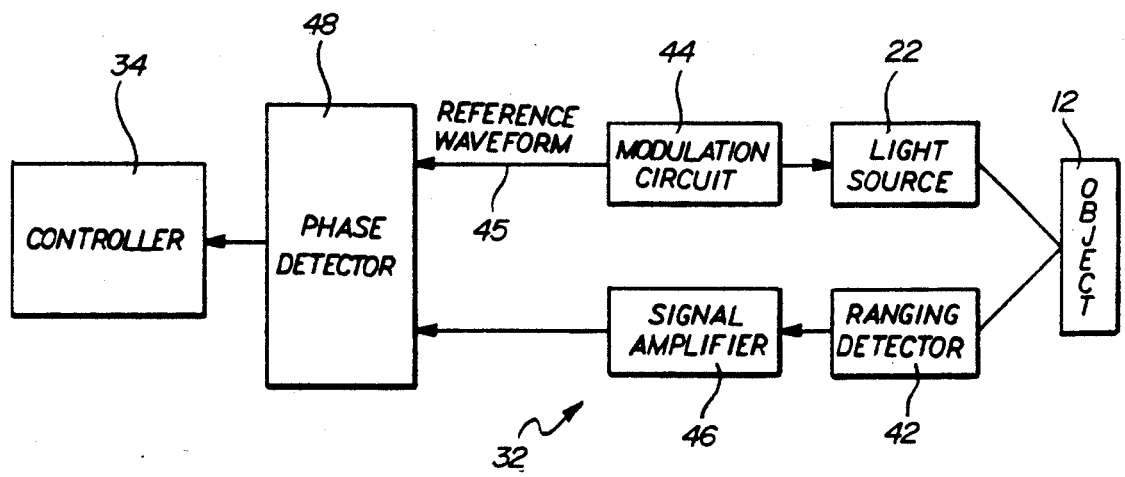

SYSTEM FOR MEASURING OPTICAL CHARACTERISTICS OF CURVED SURFACES

FIELD OF THE INVENTION

This invention relates generally to surface inspection and characterization systems, particularly to optical systems wherein a reflected beam of light is employed to analyze the characteristics of a surface. The invention most particularly relates to a system adapted for optically measuring surface characteristics of a curved, moving workpiece.

BACKGROUND OF THE INVENTION

In many manufacturing processes it is necessary to measure the surface characteristics of polished, plated, painted or otherwise finished objects. A great many measurements of surface quality may be based upon the evaluation of light reflected therefrom. Among such measurements commonly employed in manufacturing are Gloss, which is a measure of the dispersion with which light is reflected from a surface, Distinctness of Image (DOI) which is a measure of how clearly an object is reflected by the surface as well as Orange Peel and Roughness which are measurements of surface texture. There are various specific definitions accepted in the art for the foregoing terms as well as various and particular protocols for measuring or otherwise defining each of such properties, all of which can be determined in accord with the present invention by the measurement of light reflected from a surface.

There are many methods and apparatus known and available to those of skill in the art for measuring the optical characteristics of finished surfaces. In many of these methods, a beam of light is directed normal to a surface and the light reflected or scattered therefrom is measured at various angles from the normal. By determining the spatial profile of the reflected and/or scattered light, various optical properties of the surface may be determined. In other instances, the beam of light is directed at the surface at an angle of less than 90 degrees, the intensity of the reflected and/or scattered light is measured as a function of its angle and appropriate correction factors are applied to enable determination of the surface's optical properties. Such techniques are in relatively widespread use in many industries and are well-known to those of skill in the art.

Optical measurements of surface quality are valuable in a production process for quality control purposes; and obviously, it is highly desirable to fully implement such techniques in mass production processes as, for example, in the manufacture of automobiles. In order to increase efficiency of measurement and throughput of a system, it would be preferred that measurements be made "in real time," that is to say as various parts travel past a measuring station, or in some instances as a mobile measuring station scans a stationary part.

Problems are encountered in implementing such techniques because of specific geometric requirements of the optical systems. In those instances where a curved surface is being measured, care must be taken to ensure that the measuring light beam is incident to the curved surface at a precisely predefined angle. This may be readily accomplished by measuring the surface curvature and properly positioning the optical components for each point being measured. However, the time required for such repeated repositioning precludes the use of a system of this type in a continuous process. In those instances where a planar surface is being characterized, the light source and detector may be appropriately prepositioned to enable measurements to be made as the surface moves therepast; however, slight height variations, surface curvature or other irregularity will displace the reflected beam, thereby influencing the accuracy of the measurement. U.S. Pat. No. 4,139,307 discloses a surface inspection system which scans a light beam across a planar surface and spatially resolves the reflected beam to measure surface gloss. The apparatus of the '307 patent is limited in use insofar as any curvature in the surface being inspected, transverse to the direction of motion will deflect the light beam so as to prevent accurate measurement of surface quality. Likewise, U.S. Pat. No. 4,568,835 is directed to an optical inspection system for detecting contamination upon a photomask. As disclosed therein, an oblique beam of light is scanned upon a planar substrate and scattered light is detected to determine the degree of surface contamination. The particular optical system employed constricts use of the '835 invention to the inspection of strictly planar substrates.

U.S. Pat. No. 4,092,068 discloses a surface inspection sensor adapted to measure topographic features of a moving substrate. The sensor of the '068 patent illuminates a surface with a beam of light and employs a number of detectors disposed so as to receive reflected light from the surface. Variations in surface topology will cause a differential receipt of light by the various detectors and this difference can be correlated with gross surface features. The '068 patent is directed to the measurement of macroscopic features and cannot be employed for gloss, distinctness of image or other such surface measurements. Accordingly, it will be appreciated that there is a need for a system for testing the optical characteristics of surface finishes of curved, continuously moving surfaces in a production environment.

The present system provides for the rapid, economical measurement of surface characteristics of painted, plated, polished or otherwise finished surfaces and may be readily adapted for use in a continuous process and for measurement of characteristics of curved or flat surfaces. The present invention provides for a simple, economical system which repeatedly adjusts its geometry to the configurations of the surface being measured to maintain proper optical alignment. Through the use of associated data processing systems, various properties may be reliably and accurately measured. These and other advantages of the present invention will be readily apparent from the drawings, description, discussion and claims which follow.

SUMMARY OF THE INVENTION

There is disclosed herein an inspection system adapted to measure the optical characteristics of a curved surface in motion relative thereto. The system comprises a light source operative to scan a beam of light across a plurality of points on the curved surface for reflection therefrom; ranging means for measuring the distance from the light source to the point being scanned and generating a ranging signal corresponding to that distance. The system further includes a detector disposed in a fixed positional relationship relative to the remainder of the system and adapted to receive at least a portion of the reflected beam and controller means adapted to (1) receive the ranging signal, (2) compute a light path from the source to the point on the surface being scanned such that at least a portion of the light following that path will be reflected on to the detector; and (3) control of the position of the light source so as to scan the beam along the computed path.

Relative motion between the measuring system and the curved surface may be established by including a conveyor for supporting and moving the curved surface past the system or by having transport means associated with the system for moving the system past a stationary curved surface. In particular embodiments, the light source may be a collimated light source as for example a laser. The light source may be operative to scan a point beam of light across the curved surface whereas in other instances the light source may be operative to scan a planar beam of light across the surface.

The ranging means may be of the type including: a modulation circuit operative in cooperation with the light source to modulate the intensity of the beam and to also provide a reference signal corresponding to the beam modulation; a detector disposed proximate the light source adapted to receive a portion of the light reflected from the curved surface and provide a signal corresponding thereto as well as a phase detector operative to receive the reference signal from the modulation circuit and the signal from the detector, measure the phase shift therebetween and provide a ranging signal corresponding to the distance from the light source to the surface.

The detector may take the form of a plurality of photo responsive elements disposed in a linear array. In particular embodiments the array may comprise an array of amorphous silicon photovoltaic devices. In yet other embodiments, the detector may comprise a plurality of photo responsive elements arranged in a two-dimensional array.

The controller may include a computer program adapted to compute the light path. In a further embodiment, the controller may be adapted to store the parameters of the computed light path between the source and a first point being scanned, compute a second light path to a second point being scanned, store the parameters of the second light path, compare the parameters, extrapolate the curvature of the surface at a third point and control the position of the light source so as to scan the beam along a path to the third point such that at least a portion of the light beam from the source will be reflected onto the detector.

The system may include a linear detector of discrete photo responsive elements adapted to provide a signal corresponding to the spatial distribution of light reflected from the surface and may include a computer adapted to receive the signal from the detector and process that signal so as to determine at least one optical property of the surface such as Gloss, Orange Peel, or Distinctness of Image. The system may further include a chopper disposed between the light source and the detector so as to periodically interrupt the beam of light.

BRIEF DESCRIPTION OF THE DRAWINGS

FIG. 5 is a block diagram illustrating one particular ranging system which may be employed in connection with the present invention; and, FIG. 6 is a depiction of one particular linear array of photo responsive elements illustrating the projection of a reflected beam of light thereupon.

DETAILED DESCRIPTION OF THE INVENTION

Figure 1:
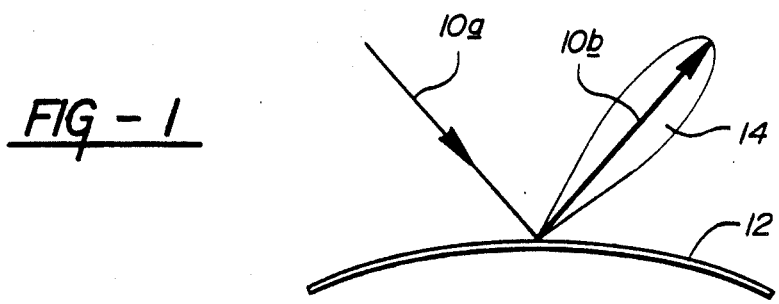
FIG. 1 is a schematic depiction of the reflection of a beam of light from a surface.

Referring now to FIG. 1 there is shown in stylized schematic form the reflection of a beam of light 10 from a surface 12. The incident beam 10a is depicted as a single ray corresponding to a highly collimated beam of finite cross section while the reflected beam 10b is noted to include a penumbra or diffuse region 14 thereabout. If the reflecting surface 12 were a perfect specular (i.e. mirror-like) surface the reflected beam 10b would retain the collimation of the incident beam 10a. However, all surfaces are somewhat irregular and tend to scatter at least a portion of the reflected beam and it is this scattered or otherwise redirected light which forms the cone-like penumbra 14. By analysis of the relative amounts of light in the specularly reflected beam 10b and the distribution of light in the penumbra 14 various optical properties of the reflecting surface 12 may be measured. For example, gloss of a surface may be quantified by measuring the amount of light in the penumbra 14 at a point generally 15 or 30 degrees deviant from the specularly reflected beam 10b. Distinctness of image is a measure of the sharpness with which an image is reflected. It is typically measured by interposing an edge in the incident light beam to cast a shadow upon the surface and measuring the sharpness of the reflected shadow by various techniques. Orange peel effect and surface roughness are generally measured by comparison of light reflected from a surface with light reflected from standard pieces; such techniques may be adapted to automated measurement by comparison of a reflectance signal with pre-established standards.

It will be apparent that a wealth of information may be gained from the profile of a reflected beam of light; however, the geometry of the incident and reflected beam must be well known so as to enable proper measurement to be made of light reflected at various deviant angles from the ideal reflected beam.

In many prior art systems, a light source and one or more detectors were disposed in a predetermined geometrical relationship and the system was precisely aligned with a reflecting surface to impinge a beam of light thereupon at a predetermined angle to allow for analysis of surface properties. Such measurements can be accurate and precise, however, positioning problems are encountered when the surface being measured is curved or otherwise irregular insofar as distortion of the angular relationships between the incident and return beam occurs; these problems are still further compounded when the surface being measured is moving. These problems are particularly severe limitations in a production mode of measurement where it is desirable to characterize work pieces at a high rate of speed.

Figure 2A:
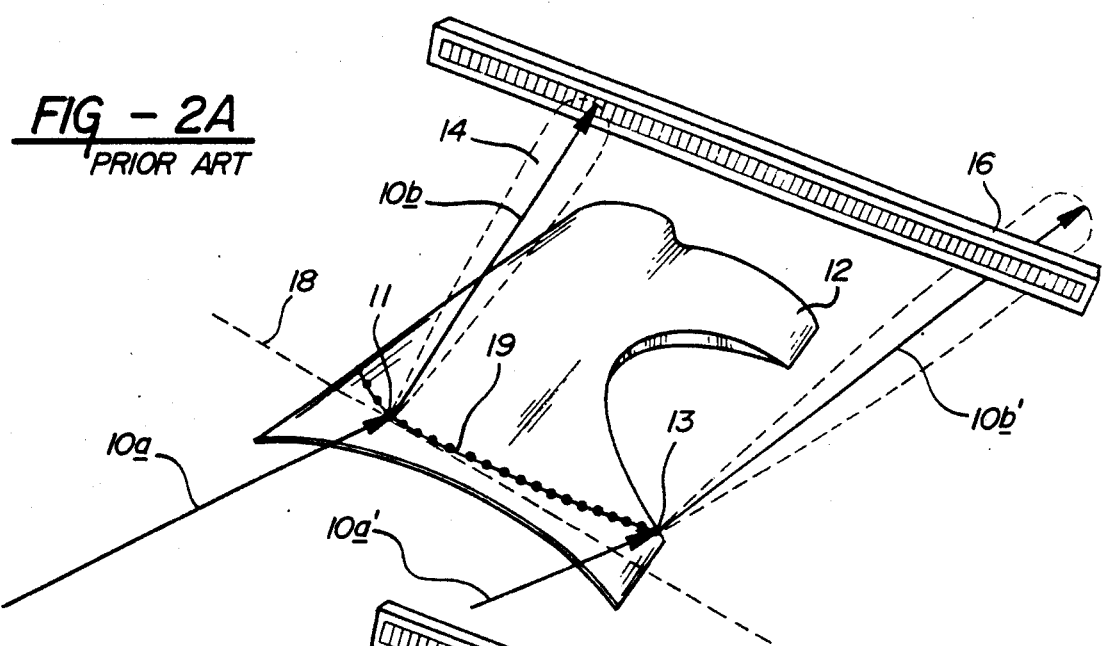
FIG. 2A is a depiction of a prior art surface inspection system illustrating problems encountered when scanning curved surfaces.

Referring now to FIG. 2A there is shown an illustration of one such group of problems encountered in the attempt to scan a beam of light across a curved work piece surface for analysis of the spatial distribution of the reflected light. As illustrated in the figure, a curved surface 12 is impinged by a first beam of light 10a which is reflected therefrom to provide a main reflected beam 10b having a somewhat diffuse penumbra 14 therearound. The geometry of the system is established such that the reflected beam 10b and its penumbra 14 fall upon a linear photo sensitive detector 16. If the detector includes a plurality of separate elements, information relating to the spatial distribution of the reflected light may be readily had. In order to measure another point along the surface, the beam of light is scanned to a new position. Scanning of the beam occurs along a generally linear path depicted by the broken line 18. If the linear scan path is followed for scanning of a planar object, the reflected light beam will remain upon the detector 16; however, when as in FIG. 2A, the surface of the object 12 being scanned is curved, scanning a beam along a linear path will produce problems. As illustrated, the linear scan path is tangent to the curved surface only at one point 11, illustrated herein as the point at which the beam 10a impinges. A second incident beam 10a' is directed toward the object 12 along the linear path 18; however, the curved surface of the object 12 falls away from this linear path. Consequently, the beam 10a' traverses a generally curved path, depicted by the dotted line 19 and impinges at a point 13 such that the reflected beam 10b' falls below the detector 16. This problem limits the use of a scanning system of this type to inspect the surface of curved or irregular objects.

Figure 2B:
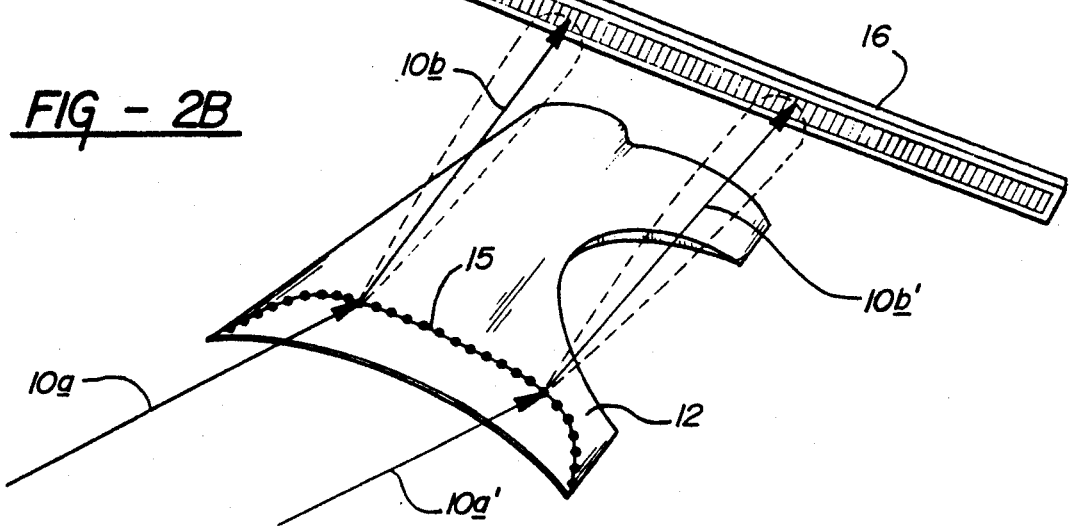
FIG. 2B is a depiction of a surface inspection system of the present invention illustrating the scanning of a curved surface.

Referring now to FIG. 2B, there is illustrated a scanning methodology in accordance with the principles of the present invention which obviates problems of the prior art. As depicted in the figure, a beam of light 10a is scanned along an object 12 in a predetermined path indicated by dotted line 15 chosen so as to maintain the reflected beam 10b on the linear detector 16 without regard to curvature. This path will correspond to the reflection of the linear detector upon the surface, from the point of view of the light source. As will be explained in greater detail herein below, the source of the light beam 10 is controlled in a closed loop system so as to scan the beam along the surface in a manner which will maintain proper illumination of the detector 16. If the object 12 is in motion relative to the light source and detector 16, scanning of its entire surface may be accomplished while maintaining the reflected beam 10b on the detector 16. By employing a methodology of this type, scanning may be rapidly and reliably accomplished without the need for repeatedly repositioning a detector.

Figure 3:
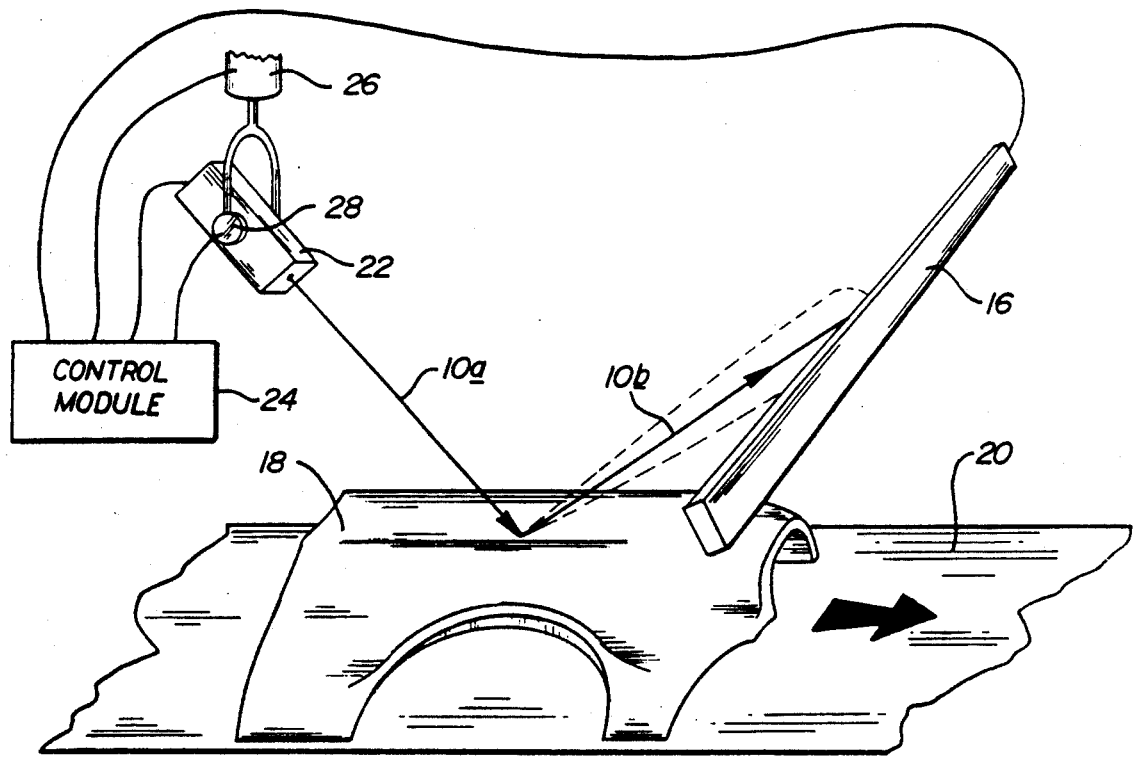
FIG. 3 is a schematic depiction of one embodiment of the present invention as adapted to inspect the surface of a moving part.

Referring now to FIG. 3, there is shown a generalized depiction of one particular scanning system structured in accord with the principles hereof as disposed to inspect the surface of automobile body panels 18 as they move along a conveyor belt 20. The system includes a light source 22, having beam steering means 26, 28 associated therewith a detector 16 and a control module 24.

The light source 22 is adapted to impinge a generally collimated beam of light 10a upon the body panel 18 and toward this end may comprise, a gas discharge lamp, an incandescent lamp or other such source and will generally include collimating optics well-known to those of skill in the art, associated therewith. Alternatively, the light source may comprise a laser. The light source may further include optical elements for shaping, filtering or otherwise conditioning the light beam as is well known to those of skill in the art. The light source 22 also preferably has associated therewith means for scanning the beam 10a across the object and toward this end will typically include a first servomotor 26 adapted to scan the light beam 10a in a direction generally transverse to the direction of motion of the body panel 18 and second servomotor or similar device 28 adapted to scan the beam of light 10a in a direction generally parallel to the direction of motion of the body panel 18. As will be noted, these scanning motors 26,28 are in electrical communication with the controller module. Beam scanning may also be accomplished optically by the use of one or more mirrors having a drive associated therewith. The light source may include a chopper or other device for modulating the light beam, and may be adapted to provide either a point beam or a planar beam.

The system further includes a detector 16 disposed in a generally fixed relationship with respect to the rest of the scanning system. The detector 16 is positioned so as to receive at least a portion of the reflected beam of light 10b from the body panel 18. As depicted, the detector 16 is disposed generally transverse to the direction of travel of the body panel and if that body panel were perfectly planar, simple scanning of the light source 22 with the servoscanner 26 would sweep the reflected beam 10b across the length of the detector 16, as the panel travels past. Since the panel is not planar, simple linear scanning will not suffice (c.f. FIG. 2a), therefore the light source is controlled, to maintain reflected light upon the detector 16, as the curved panel travels along the conveyors.

The detector 16 is advantageously configured as a linear array comprised of a plurality of discrete photo responsive elements. Such photo responsive elements may take the form of photo conductive elements adapted to change their electrical resistivity in response to illumination thereof or photovoltaic elements adapted to generate a flow of electrical current in response to illumination.

Figure 6:
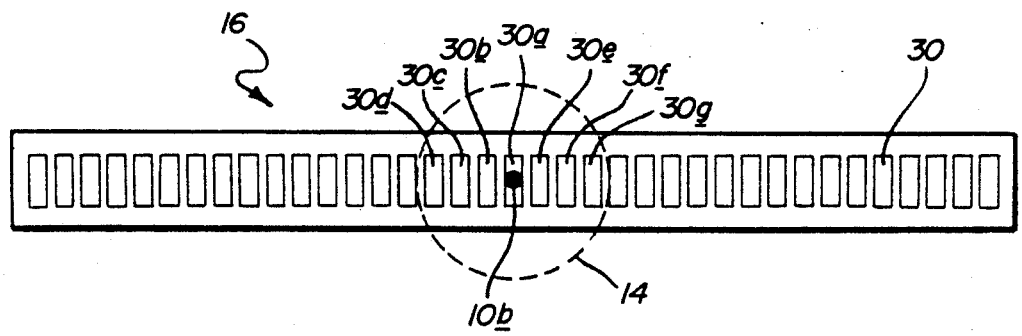

Referring now to FIG. 6, there is shown one particular configuration of detector 16 which may be employed in the practice of the present invention. As shown in the figure, the detector 16 includes a plurality of discrete elements, as for example, element 30. Such elements are disposed in spaced-apart relationship and each is adapted to provide a separate signal indicative of the illumination thereof. In those instances where the elements 30 are photo conductive elements they may advantageously be fabricated from a material such as cadmium sulfide or silicon. In those instances where the photo responsive elements 30 are photovoltaic elements they may each comprise a silicon or a germanium photovoltaic device. Recent advances have been made in the fabrication of thin film arrays of photovoltaic and/or photo conductive devices from amorphous alloys of silicon and germanium as disclosed in U.S. Pat. No. 4,226,898, and such devices may be advantageously employed in connection with this invention.

FIG. 6 also depicts the impingement of a beam of reflected light upon the detector array. As shown, the reflected beam includes the main beam 10b represented by a dark circle and the penumbra of the beam 14 depicted by the broken circle. The central portion of the reflected beam falls upon the detector array and the main portion of the reflected ray 10b is incident upon detector element 30a and strongly illuminates that element. The penumbral portion of the beam 14 falls upon detectors 30b–30g and illuminates them less strongly. Output from the detector array will then comprise a relatively high level signal from centrally illuminated detector 30a and lower level signals from detectors 30b–30g. Difference in intensity registered by detectors 30b, 30c and 30d for example will indicate the profile of the reflected light and may be processed as is well known by those of skill in the art to derive information relating to gloss, distinctness of image and the like.

It should be noted that while the detector elements 30 are shown as being of a particular size such that the central beam 10b illuminates a single element 30a, this obviously need not be the case, for example, through the use of conventional photolithographic techniques in conjunction with thin film device fabrication methodology, an array of photo responsive elements of micron scale size may be fabricated and in such instance it will be anticipated that the central portion of the beam 10b will illuminate a number of detectors. It is also anticipated that the detector array may be fabricated as a two-dimensional array, that is to say that an array of N X M devices wherein both N and M are greater than 1. In such instance signal generation and processing will be analogous to that previously described.

It will be appreciated from a perusal of FIG. 6 that success of a measuring technique of this type depends upon proper positioning of the detector with respect to the reflected beam. If for example, the beam is off-center with respect to the detector the central portion 10b will fall outside of the sensitive area of the measuring elements and only the penumbral portion 14 will be sensed, leading to erroneous readings. Accordingly, the present invention compensates for irregularities in the reflecting surface and adjusts the light source so as to maintain the reflected beam in proper orientation with respect to the detector array.

Figure 4:
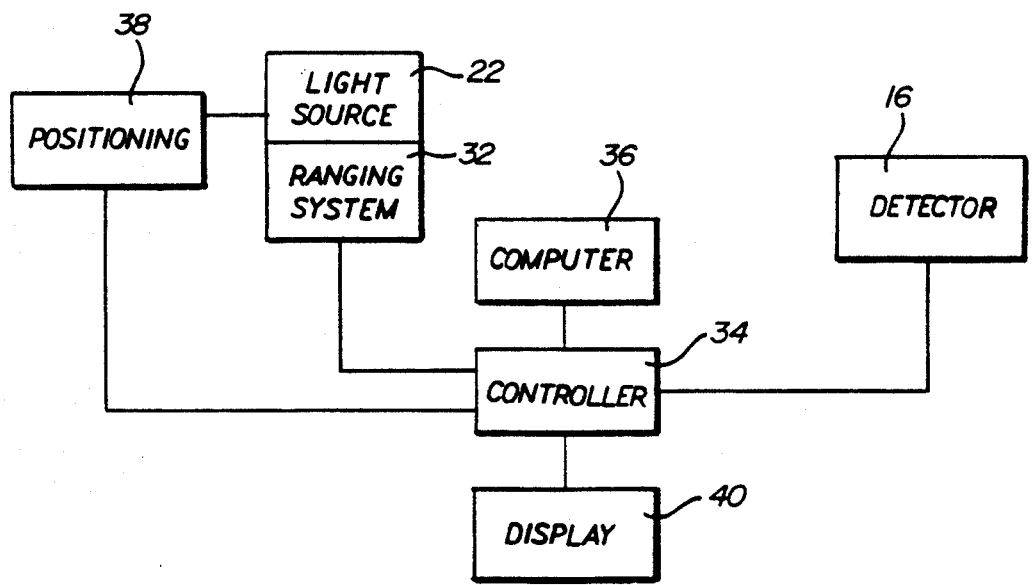
FIG. 4 is a block diagram of one embodiment of the present invention.

Referring now to FIG. 4, there is shown a block diagram including the major operational components of one scanning system of the present invention as for example the system depicted in FIG. 3. The system includes a light source 22 and detector 16 as previously described. The system further includes positioning means 38, a ranging system 32, a computer 36, a controller 34 and a display 40, which collectively comprise the control module 24 described with reference to FIG. 3; it being understood that this control module 24 may comprise a greater or lesser number of such sub elements.

The ranging system 32 is operational to determine the distance from the light source 22 to the object being scanned and generate a ranging signal corresponding to that distance. There are available various technologies for accomplishing the ranging including sonic and ultrasonic techniques as well as purely optical techniques, as will be described in greater detail hereinbelow. The ranging system 32 is in electrical communication with a controller 34, preferably having a computer 36 associated therewith. The controller 34 receives ranging signals and computes a light path from the source 22 to the point on the surface of the object being scanned such that at least a portion of the light following that path will be reflected onto the detector. The parameters of this computed path may be stored in the computer 36 for later reference and the controller 34 controls a positioning means 38 associated with the light source 22 so as to direct the beam therefrom along the computed path.

The controller 34 is also in electrical communication with the detector 16 and is adapted to receive signals therefrom indicative of the profile of the reflected light. The controller 34 conveys the detector signals to the computer 36 for calculation of the various optical parameters of the surface through the use of predetermined measurements protocols. For example, it may be empirically determined that orange peel effect is quantified by the measurement of light at an angle "Alpha" from the specularly reflected beam, thus by measurement of penumbral intensities such effect may be measured. Likewise, other optical properties may be calculated utilizing well-known techniques. The computer 36 may also be programmed to recognize and signal an error condition, as for example when the light beam is not reflected directly onto the detector array. The controller may also preferably have associated therewith display means 40 such as a cathode ray tube, liquid crystal display or printer for presenting results of the measurement in a human readable form.

As mentioned previously, there are a variety of light sources and ranging systems available. One system having particular utility is a system such as that disclosed in U.S. Pat. No. 4,569,078 of Zuk entitled "Image Sensor", the disclosure of which is incorporated herein by reference. The system of Zuk discloses method and apparatus for illuminating an object with a beam of light, measuring the phase shift in the reflected beam so as to determine the distance to the object and controlling the light beam in response to the measured distance. Referring now to FIG. 5, there is shown in block diagram form a ranging system 32 corresponding to that described in Zuk and adapted for use in the present invention. The system 32 includes a light source 22 which includes a laser or other collimated source disposed so as to illuminate an object 12. Physically associated with the light source 22 is a ranging detector 42 which may comprise a photo diode or similar photo responsive device adapted to provide an output signal as a function of light received from the object 12.

A modulation circuit 44 is employed for modulating the light source 22. In one particular embodiment, the light source 22 is a gas discharge laser and the modulation circuit 44 employs conventional "mode locking" techniques to modulate the amplitude of the laser by using acousto-optical devices. The modulation circuit 44 is also adapted to supply a reference wave form 45 at its output, which reference wave form is a function of the signal used to modulate the light source 22. In another embodiment, the light source is a diode laser and the modulation circuit 44 controls the output of that laser by controlling the power supplied thereto, and as in the gas discharge embodiment provides a corresponding reference waveform 45. Modulation of a continuous wave beam may also be accomplished by the use of an electro-mechanical chopper which is also operative to provide a reference waveform.

The output of the ranging detector 42 is amplified by a signal amplifier 46 and together with the reference wave form from the modulation circuit 44 is conveyed to a phase detector 48.

The phase detector 48 compares the signal from the ranging detector with the reference wave form 45. The difference between these two signals is a function of the distance between the detector 42 and the object 12. The output of the phase detector 48 is conveyed to the controller 34 and the light source 22 may be controlled accordingly, so as to select a distance which will reflect the incident beam onto the detector. One of skill in the art will be aware of various embodiments and circuitry for detecting difference in the two phases, and the aforementioned patent of Zuk discloses such circuitry in detail.

In this manner, the present invention is adapted to control a light source so as to permit scanning of an object while maintaining a light beam reflected from that object upon a fixed detector array without regard to curvature or other irregularity in the object. In a further refinement of the present invention, the controller and computer may be adapted to: (1) store the parameters of a first light path computed from the light source to a first scanned point on the object with a second set of parameters corresponding to a second computed light path from the source to a second point on the object, (2) extrapolate the curvature of the object therefrom and (3) direct the light beam along a third computed path to a third scan point. This particular embodiment is well-suited for accommodating curvature in the direction parallel to the motion of the object past the scanning system. It has also been found advantageous to further adapt the measuring system to "find" parts moving toward it on a conveyor belt. Such finding can be readily accomplished by adapting the controller to rapidly scan the light source across the conveyor until a reflected signal is detected which is indicative that a part is within range. Once a part is detected, a systematic scan of its surface may be implemented as discussed previously.

There will obviously be other variations readily apparent to one of skill in the art. As mentioned previously, the entire scanning system may be mounted so as to allow it to be moved past a relatively stationary object. Such an embodiment is particularly well-suited for the scanning of relatively large or otherwise difficult to move objects.

In light of the foregoing, it is apparent that many modifications and variations will be apparent to one of skill in the art. Accordingly, the foregoing drawings, discussion and description are merely meant to be illustrative of particular embodiments of the present invention and not limitations upon the practice thereof. It is the following claims, including all equivalents, which define the scope of the invention.

I claim:

1. An inspection system adapted to measure optical characteristics of a curved surface in motion relative thereto, said system comprising:
   a light source operative to scan a beam of light across a plurality of points on the curved surface for reflection therefrom;
   ranging means for measuring the distance from the light source to the point being scanned and generating a ranging signal corresponding thereto;
   a photo detector disposed in a fixed positional relationship relative to a transverse direction to the motion of the curve surface and adapted to receive at least a portion of the reflected beam;
   controller means adapted to: (1) receive said ranging signal, (2) compute parameters of a light path from the source to the point on the surface being scanned such that at least a portion of the light following that path will be reflected onto the detector and (3) control the position of the light source so as to scan the beam along the computed path.

2. A system as in claim 1, further including a conveyer for supporting and moving the curved surface whereby relative motion between that surface and the system is established.

3. A system as in claim 1, further including transport means for moving the system past a stationary curved surface whereby relative motion therebetween is established.

4. A system as in claim 1, wherein the light source is a collimated light source.

5. A system as in claim 1, wherein the light source includes a laser.

6. A system as in claim 1, wherein the light source is operative to scan a point beam of light.

7. A system as in claim 1, wherein the light source is operative to scan a planar beam of light.

8. A system as in claim 1, wherein said ranging means includes:
   a modulation circuit operative in cooperation with the light source to modulate the intensity of the beam and provide a reference signal corresponding to said beam modulation;
   a detector disposed proximate the light source and adapted to receive a portion of the light reflected from the curved surface and provide a signal corresponding thereto; and
   a phase detector operative to receive the reference signal from the modulation circuit and the signal from the detector, measure the phase shift therebetween, and provide a ranging signal corresponding to the distance from the light source to the surface.

9. A system as in claim 1, wherein said detector comprises a plurality of photoresponsive elements disposed in a linear array.

10. A system as in claim 1, wherein said detector comprises an array of amorphous silicon photovoltaic devices.

11. A system as in claim 1, wherein said detector comprises a plurality of photoresponsive elements arranged in a two-dimensional array.

12. A system as in claim 1, wherein said controller means includes a computer programmed to compute said light path.

13. A system as in claim 12, wherein the detector is a linear array of discrete photoresponsive elements adapted to provide a signal corresponding to the spatial distribution of light reflected from the surface and wherein the computer is adapted to receive the signal from the detector and is further programmed to process that signal so as to determine at least one optical property of the surface.

14. A system as in claim 13, wherein the computer is programmed to determine gloss of the surface from the spatial distribution of reflected light.

15. A system as in claim 13, wherein the computer is programmed to determine "orange peel" from the spatial distribution of the reflected light.

16. A system as in claim 13, wherein the computer is programmed to determine the distinctness of image from the intensity profile of reflected light.

17. A system as in claim 1, further including a chopper disposed between the light source and the detector so as to periodically interrupt the beam of light.

18. An inspection system as in claim 1, wherein said controller is further adapted to store the parameters of the computed light path between the source and a first point scanned, compute a second light path to a second point scanned, store the parameters of said second light path, compare said parameters, extrapolate the curvature of the surface at a third point and control the position of the light source so as to scan the beam along a path to the third point such that at least a portion of the light beam from the source will be reflected onto the detector.

19. An inspection system adapted to measure optical characteristics of a curved surface in motion relative thereto, said system comprising:
   a light source operative to scan a beam of collimated light across a plurality of points on the curved surface for reflection therefrom;
   a ranging system including: a modulation circuit operative to modulate the intensity of the beam of light and provide a reference signal corresponding to said modulation; a first photo detector disposed proximate the light source and adapted to receive a portion of the light reflected from the curved surface and provide a signal corresponding thereto, and a phase detector operative to receive the reference signal and the signal from the detector, measure the phase shift therebetween and provide a ranging signal corresponding to the distance from the light source to the surface;
   a second photo detector comprised of a linear array of photoresponsive elements disposed in a fixed positional relationship relative to a transverse direction to the motion of the curve surface and adapted to receive at least a portion of the reflected beam;
   a controller adapted to (1) receive the ranging signal (2) compute a light path from the light source to the surface being scanned such that at least a portion of the light following that path will be reflected onto the second photo detector and (3) control the position of the light source so as to scan the beam along the computed path.

20. A method for measuring the optical characteristics of a curved surface by detecting the characteristics of a beam of light reflected therefrom, said method including the steps of:
   providing a light source operative to scan a beam of light across a plurality of points on the curved surface;
   providing a ranging system for measuring the distance form the light source to the point being scanned and generating a ranging signal corresponding thereto;
   providing a photo detector operative to receive light reflected from said curved surface and to provide a signal corresponding to the characteristics of said reflected light;
   providing controller adapted to: (1) receive the ranging signal from the ranging system, (2) compute a light path from the source to the point on the surface being scanned such that at least a portion of the light following the path will be reflected onto the photo detector and (3) control the position of the light source so as to scan the beam along the computer path; and
   analyzing the signal from the photo detector so as to determine the optical characteristics of the curved surface.

* * * * *